United States Patent
De Vos et al.

(10) Patent No.: US 11,952,321 B2
(45) Date of Patent: Apr. 9, 2024

(54) METHOD FOR THE HYDRODEOXYGENATION OF OXYGENATED COMPOUNDS TO UNSATURATED PRODUCTS

(71) Applicant: TOTALENERGIES ONETECH BELGIUM S.A., Seneffe (BE)

(72) Inventors: Dirk De Vos, Holsbeek (BE); Maxime Stalpaert, Lummen (BE)

(73) Assignee: TOTALENERGIES ONETECH BELGIUM S.A., Seneffe (BE)

( * ) Notice: Subject to any disclaimer, the term of this patent is extended or adjusted under 35 U.S.C. 154(b) by 335 days.

(21) Appl. No.: 17/622,456

(22) PCT Filed: Jun. 26, 2020

(86) PCT No.: PCT/EP2020/068033
§ 371 (c)(1),
(2) Date: Dec. 23, 2021

(87) PCT Pub. No.: WO2020/260588
PCT Pub. Date: Dec. 30, 2020

(65) Prior Publication Data
US 2022/0356126 A1    Nov. 10, 2022

(30) Foreign Application Priority Data

Jun. 28, 2019 (EP) .................... 19183334

(51) Int. Cl.
| | | |
|---|---|---|
| *C07C 1/207* | (2006.01) | |
| *B01J 23/46* | (2006.01) | |
| *C07C 1/24* | (2006.01) | |
| *C07C 45/49* | (2006.01) | |
| *C07D 307/36* | (2006.01) | |

(52) U.S. Cl.
CPC .............. *C07C 1/24* (2013.01); *B01J 23/462* (2013.01); *C07C 45/49* (2013.01); *C07D 307/36* (2013.01); *C07C 2523/46* (2013.01)

(58) Field of Classification Search
CPC ......... C07C 1/207; C07C 1/24; C07D 307/36; B01J 23/462
See application file for complete search history.

(56) References Cited

FOREIGN PATENT DOCUMENTS

| | | |
|---|---|---|
| JP | 2016056147 A | 4/2016 |
| WO | 2013090070 A1 | 6/2013 |

OTHER PUBLICATIONS

International Search Report dated Sep. 21, 2020 in reference to co-pending European Patent Application No. PCT/EP2020/068033 filed Jun. 26, 2020.
Written Opinion dated Sep. 21, 2020 in reference to co-pending European Patent Application No. PCT/EP2020/068033 filed Jun. 26, 2020.
Di Mondo, et al., "Stainless Steel as a Catalyst for the Total Deoxygenation of Glycerol and Levulinic Acid in Aqueous Acidic Medium", American Chemical Society, vol. 1, pp. 355-364, 2011.
Hu, et al., "Solid Acid-Catalyzed Dehydration of Pinacol Derivatives in Ionic Liquid: Simple and Efficient Access to Branched 1,3-Dienes", American Chemical Society, vol. 7, pp. 2576-2582, 2017.
Stalpaert, et al., "Conversion of lactide to acrylic acid by a phosphonium ionic liquid and acid cocatalyst", Catalysis Science & Technology, vol. 8, pp. 1468-1474, 2018.
Stalpaert, et al., "Tetrabutylphosphonium Bromide Catalyzed Dehydration of Diols to Dienes its Application in the Biobased Production of Butadiene", American Chemical Society, vol. 7, pp. 5802-5809, 2017.
Stalpaert, et al., "Tetrabutylphosphonium Bromide: A versatile ionic liquid catalyst for the bio-based production of butadiene and acrylic acid", 255th ACS National Meeting, p. 1, 2018.
Stalpaert, et al., "Tetrabutylphosphonium Bromide: A versatile ionic liquid catalyst for the bio-based production of butadiene and acrylic acid", Center for Surface Chemistry and Catalyst, pp. 1-2, 2017.
Thibault, et al., "Cyclopentadienyl and pentamethylcyclopentadienyl ruthenium complexes as catalysts for the total deoxygenation of 1,2-hexanediol and glycerol", Green Chemistry, vol. 13, pp. 357-366, 2011.
Zhang, et al., "Low temperature dehydrations of non-activated alcohols via halide catalysis", Organic Chemistry, vol. 3, pp. 701-708, 2016.
STALPAERT,, "Deoxygenation of Polyols and Rearrangement of Lactide by Homogeneous and Ionic Liquid Catalysts", pp. 1-174, Oct. 2018.

*Primary Examiner* — Sikarl A Witherspoon
(74) *Attorney, Agent, or Firm* — Ewing & Jones, PLLC

(57) ABSTRACT

The invention relates to methods of hydrodeoxygenation of oxygenated compounds into compounds with unsaturated carbon-carbon bonds, comprising the steps of: a) providing a reaction mixture comprising, an oxygenated compound containing one or more of a hydroxyl, keto or aldehyde group, an ionic liquid, a homogeneous metal catalyst, and carbon monoxide or a carbon monoxide releasing compound, b) reacting said reaction mixture under a H2 atmosphere at acidic conditions at a temperature between 180 and 250° C. and a pressure between 10 and 200 bar.

9 Claims, No Drawings

METHOD FOR THE HYDRODEOXYGENATION OF OXYGENATED COMPOUNDS TO UNSATURATED PRODUCTS

CROSS REFERENCES TO RELATED APPLICATIONS

This application is a national-stage application under 35 U.S.C. § 371 of International Application No. PCT/EP2020/068033, filed Jun. 26, 2020, which International Application claims benefit of priority to European Patent Application No. 19183334.2, filed Jun. 28, 2019.

FIELD OF THE INVENTION

The invention relates to the processing of biomass, more particular the conversion of sugar alcohols to olefins.

BACKGROUND OF THE INVENTION

Biomass attracts significant attention as a renewable raw material for the production of chemicals. However, the most abundant biomass is severely overfunctionalized for most industrial applications. For example, sugar alcohols have around 1 oxygen atom per carbon. They are an important group of biobased compounds of which several can be produced on a relatively large scale. Glycerol is produced as a large scale side product in the production of biodiesel, while erythritol can be produced by fermentation of glycerol or glucose. Pentitols and hexitols, in particular xylitol and sorbitol can be formed by splitting and reduction of the most abundant biopolymers, cellulose and hemicellulose. Hence, these and other sugar alcohols could be interesting biobased substrates for the production of industrial chemicals.

An attractive option is to convert these sugar alcohols into olefins, which are valuable industrial compounds. Propylene is the second most important starting compound in the chemical industry after ethylene, as it is used in the production of polypropylene, propylene oxide, acrylonitrile, cumene, butyraldehyde, acrylic acid, acetone and many others. Butenes, pentenes and hexenes are valuable intermediates for industry; in particular the α-olefins are highly important co-monomers. It is however very challenging to perform the conversion of sugar alcohols to olefins selectively. The defunctionalization of polyols to olefins is in principle possible by a combination of dehydration and hydrogenation, which can be described as hydrodeoxygenation; however most hydrogenation catalysts reduce C=C bonds much faster than C=O or C—O bonds. Consequently, it is hard to stop the defunctionalization at the olefin stage under a $H_2$ pressure, and alkanes are the typical, but much less valuable products of hydrodeoxygenation of polyols.

The use of ionic liquids as catalysts for dehydration reactions has been reported. Zhang et al. ((2016) *Org. Chem. Front.* 3, 701) have used tetrabutylammonium bromide for dehydration of several mono-alcohols to alkenes, Hu et al. ((2017) ACS Catal. 7, 2576-2582) have reported 3-methylimidazolium chloride for (double) dehydration of pinacol derivatives to conjugated dienes and Stalpaert et al. (2017) ACS Catal. 7, 5802-5809) have used tetrabutylphosphonium bromide for dehydration of several mono-alcohols to alkenes, diols to conjugated dienes. Stalpaert et al. (2018) *Catal. Sci. Technol.* 8, 1468) reported dehydration of lactic acid to acrylic acid and rearrangement of lactide to acrylic acid. The presence of an active hydrogenation catalyst in these systems has not been reported. Hence, these systems are not capable of hydrodeoxygenating polyols or sugar alcohols to olefins. Homogeneous Ru catalysts have been used for hydrodeoxygenation of glycerol to propylene. Thibault et al. (2011) *Green Chem.* 13, 357) reported the use of Ru cyclopentadienyl and pentamethylcyclopentadienyl complexes together with triflic acid in sulfolane at 200° C. and 48 bar $H_2$. The propene yield in this reaction is not quantified. Di Mondo et al. (2011) ACS Catal. 1, 355-364) reported the formation of propylene from glycerol using triflic acid and $[Ru(H_2O)_3(4'$-phenylterpyridine$)](OTf)_2]$ as catalysts in water at 250° C. under 55 bar $H_2$. In these conditions, the 316SS stainless steel of the reactor is corroded, leading to the formation of mixed chromium oxides, which are the real active hydrogenation catalyst in this reaction. A yield of 100% is reported by attributing the mass loss from the liquid phase to propylene. Hydrodeoxygenation of polyols other than glycerol is not reported. These systems do not use an ionic liquid or CO releasing molecule, which are both highly beneficial for product yield and selectivity, and allow a broader substrate scope. Using an ionic liquid allows working with less corrosive acids.

Stalpaert et al. (Abstracts of Papers, 255th ACS National Meeting & Exposition 2018, CATL-265 & Abstracts of Posters, TOCAT8 2018, P1065) have reported the combined hydrogenation and dehydration of sugar alcohols to olefins by a combination of the ionic liquid tetrabutylphosphonium bromide and a transition metal catalyst. The substrate scope, product yields and selectivities are not disclosed. There is no suggestion of the homogeneity of the transition metal catalyst, the use of Ru(II) or Ru(III) species, or of CO releasing molecules. As the examples in this invention illustrate, the use of homogeneous Ru(II) or Ru(III) species and the presence of CO releasing molecules are highly beneficial for product yields and selectivity.

The state of the art lacks a selective catalyst for the conversion of sugar alcohols to olefins, for example through combined dehydration and selective C=O hydrogenation.

SUMMARY OF THE INVENTION

The present invention provides a catalytic system that can be used for complete removal of ketone, aldehyde, acetal or hydroxy group from an organic substrate, leading to C=C unsaturated compounds, especially if the system is tolerant towards other oxygen containing functionalities, such as carboxylic acids. Hence, other substrates containing these functionalities are also attractive substrates. For example, levulinic acid, which is produced by acid treatment of glucose or fructose, or its esters can be converted to pentenoic acids or esters, which could potentially be used to produce adipic acid, adiponitrile or caprolactam. Other biobased substrates of interest include sugar acids, such as glucaric acid, and pyrolysis oil. Other suitable substrates include non-biobased compounds containing ketone, aldehyde or hydroxy groups, referred to as oxygenated compounds. The present invention describes a novel method for the deoxygenation of oxygenated compounds, compounds containing carbon-carbon unsaturated bonds, such as alkenes, dienes and unsaturated carboxylic acids. The process can be performed under a pressure of $H_2$ without overreduction to alkanes or saturated carboxylic acids.

The invention is further summarized in the following statements:

1. A method of hydrodeoxygenation of oxygenated compounds into compounds with unsaturated carbon-carbon bonds, comprising the steps of:

a) providing a reaction mixture comprising,
an oxygenated compound containing one or more of a hydroxyl, keto or aldehyde group,
an ionic liquid
a homogeneous metal catalyst
carbon monoxide or a carbon monoxide releasing compound,
b) reacting said reaction mixture under a H2 atmosphere at acidic conditions at a temperature between 180 and 250° C. and a pressure between 10 and 200 bar.

2. The method according to statement 1, wherein the carbon monoxide releasing compound is formaldehyde.

3. The method according to statement 1 or 2, wherein the oxygenated compound is a sugar or a sugar alcohol.

4. The method according to any one of statements 1 to 3, wherein the ionic liquid cation is a phosphonium, such as tertrabutylphosphonium.

5. The method according to any one of statements 1 to 4, wherein the ionic liquid anion is bromide.

6. The method according to statement any one of statements 1 to 5, wherein the metal catalyst is metallic ruthenium or a compound comprising Ru(II) or Ru(III).

7. The method according to any one of statements 1 to 6, wherein the CO releasing compound is an aldehyde, a carboxylic acid or a metal carbonyl.

8. The method according to statement 7, wherein the metal carbonyl is the CO releasing compound and comprises the metal catalyst.

DETAILED DESCRIPTION OF THE INVENTION

The present invention demonstrates that a system comprising an ionic liquid, an acidic compound and a homogeneous metal complex can catalyze under hydrogen pressure the hydrodeoxygenation of several oxygenated compounds such as sugar alcohols, into products with unsaturated carbon-carbon bonds.

The selective production of unsaturated compounds is achieved by heating an oxygenated compound under a $H_2$ atmosphere in the presence of three catalysts:

1) An ionic liquid (IL) having the formula [Cat$^+$][X$^-$], wherein [Cat$^+$] represents one or more organic cationic species, and [X$^-$] represents one or more anionic species
2) An acidic compound,
3) A homogeneous metal species,
4) carbon monoxide or a carbon monoxide releasing compound.

An "oxygenated compound" is a molecule containing one or more functional groups of which at least one is a hydroxyl, keto or aldehyde group.

The oxygenated compound can be a sugar alcohol including, but not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol and polyglycitol.

The oxygenated compound can be a sugar, a sugar acid, such as tartaric acid, glucaric acid, levulinic acid, gamma-valerolactone, alpha-angelicalactone, beta-angelicalactone, hydroxymethylfurfural or furfural.

The reaction can also be performed on a mixture of oxygenated compounds. One non-limiting example of such a mixture is pyrolysis oil.

By "catalyst" is meant a compound which participates in the reaction, but is not stoichiometrically changed in it, i.e. which is not consumed by the reaction.

By "ionic liquid" is meant an organic salt which is liquid at the temperature used for the desired reaction and preferably, has a melting temperature of at least 10° C. below the temperature used for the desired reaction.

The term "a catalyst comprising an ionic liquid" refers to a pure ionic liquid, as well as but also to an ionic liquid incorporated in the catalyst, which may hence be solid. For example, the ionic liquid may be impregnated in or on a carrier. Also, the IL may be a polymerized monomer. Since many ionic liquids are corrosive in the reaction conditions of the invention, a solid carrier like silica, alumina, titania, zirconia or another stable oxide can be used.

The ionic liquid can also be used as a mixture with an inert compound (which does not react in the reaction conditions of the invention) or with one of the reagents. In that case, the ionic liquid concentration in the mixture is preferably at least 5%, more preferably at least 10% molar.

According to the invention, the cation [Cat$^+$] is an organic cation which may for instance be of the phosphonium, ammonium or sulfonium type, or also of heteroaromatic nature.

The cation [Cat$^+$] can be a phosphonium ion with the following general formula [PRaRbRcRd]$^+$, wherein Ra, Rb, Rc, Rd are independently chosen from the group consisting of alkyl (with C1 to C30 typically C1 to C16), aryl (C6 to C10), arylalkyl, heteroaryl, heteroarylalkyl or hydrogen; whereby one or more of alkyl, aryl, arylalkyl, heteroaryl, heteroarylalkyl groups are optionally substituted with a (cyclo)alkyl, (cyclo)alkoxy, aryl, arylalkyl, amide, ammonium or phosphonium group.

The cation [Cat$^+$] can also be an ammonium ion of the type [NR$_a$R$_b$R$_c$R$_d$]$^+$ wherein R$_a$, R$_b$, R$_c$, R$_d$ are independently selected from the group consisting of alkyl (with C1 to C30), aryl (C6 to C10), arylalkyl, heteroaryl, heteroarylalkyl or hydrogen; whereby one or more of the alkyl, aryl, arylalkyl, heteroaryl, heteroarylalkyl groups optionally substituted a with (cyclo)alkyl, (cyclo)alkoxy, aryl, arylalkyl, amide, ammonium and phosphonium group.

The cation [Cat$^+$] can also be a sulfonium ion of the type [SR$_a$R$_b$R$_c$]$^+$ wherein R$_a$, R$_b$, R$_c$ are independently selected from the group consisting of alkyl (with C1 till C30), aryl (C6 to C10), arylalkyl, heteroaryl, heteroarylalkyl or hydrogen; whereby one or more of the alkyl, aryl, arylalkyl, heteroaryl, heteroarylalkyl groups are optionally substituted with (cyclo)alkyl, (cyclo)alkoxy, aryl, arylalkyl, amide, ammonium and phosphonium groups.

The cation [Cat$^+$] can also be of heteroaromatic nature, with N or P atoms in the aromatic ring, whereby the ring is selected form the group consisting of imidazolium, pyridinium, pyrrolidinium, benzimidazolium, phthalazinium, piperidinium, pyrrolium, quinazolinium, quinolinium, isoquinolinium, indolinium and indolium type.

Typically, the cation is of the phosphonium type [PR$_a$R$_b$R$_c$R$_d$]$^+$. It has been found that ionic liquids with such a cation show superior thermal stability under the reaction conditions.

More typically, the substituents R$_a$, R$_b$, R$_c$, R$_d$ of this phosphonium cation are independently selected the group consisting of a linear or branched alkyl, aryl, arylalkyl group, consisting exclusively of C and H atoms, and hydrogen. In addition, the substituents R$_a$, R$_b$, R$_c$ and R$_d$ are optionally mutually connected through carbon-carbon bonds.

Typical phosphonium type cations include but are not limited to tetrabutylphosphonium or Bu$_4$P$^+$, methyl-tributylphosphonium or Bu$_3$MeP$^+$, tributylphosphonium or Bu$_3$HP$^+$, tributyl(tetradecyl)phosphonium or Bu$_3$TetradecP and trihexyl(tetradecyl)phosphonium or $Hex_3(Tetradec)P^+$. $Bu_4P^+$ is preferred because ionic liquids with this cation show the best catalytic performance and some are readily commercially available, such as $Bu_4PBr$ and $Bu_4PCl$ under the respective brand names Cyphos® 442W and Cyphos® 443P from the company Solvay.

The anion $[X^-]$ can be either an organic or inorganic anion. Non-limiting examples of organic cations are carboxylates (e.g. acetate, lactate, decanoate, benzoate, amino acids), alkylsulfates, alkylphosphates, alkylphosphinates, tosylates and methanesulfonate. Preferably, the anion is inorganic; non-limiting examples are chloride ($Cl^-$), bromide ($Br^-$), iodide ($I^-$), nitrate ($NO_3^-$), tetrafluoroborate ($BF_4^-$), hexafluorophosphate ($PF_6^-$), triflate ($CF_3SO_3^-$), and bis(trifluoromethylsulfonyl)imide (($CF_3SO_3)_2N^-$). Even more preferably, the anion is $Br^-$.

In the present invention, the catalyst may comprise mixtures of ionic liquids as described in the above.

The acidic compound can be either a Brønsted or a Lewis acid and can be homogeneous or heterogeneous. Non-limiting examples are acetic acid ($CH_3CO_2H$) and other organic acids, phosphoric acid ($H_3PO_4$), pyrophosphoric acid ($H_4P_2O_7$), sulfuric acid ($H_2SO_4$), hydrobromic acid (HBr), hydrochloric acid (HCl), hydroiodic acid (HI), nitric acid ($HNO_3$), Lewis acids based on e.g. $Ca^{2+}$, $Mg^{2+}$, $Al^{3+}$, $Cu^{2+}$, $Fe^{3+}$, $Sc^{2+}$, and $Ln^{3+}$, sulfonated polymers (e.g. Nafion), heteropolyacids, silica ($SiO_2$), alumina ($Al_2O_3$), silica-alumina ($SiO_2$—$Al_2O_3$), titania ($TiO_2$), zirconia ($ZrO_2$) and zeolites. Also mixtures of different acidic compounds can be used. Preferably, the acidic compound is a strong, hard acid, typically with a $pK_a<-2$. Preferably the acid is not volatile and The homogeneous metal species is formed in the reaction conditions from a metal-containing precursor. A suitable metal-containing precursor is any metal compound that, at least partially, forms a dissolved metal species in the reaction conditions. The metal is preferably from block IVB, VB, VIB, VIIB, VIIIB or IB, namely titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, or gold; more preferably chromium, manganese, rhenium, iron, ruthenium, cobalt, rhodium, iridium, nickel, palladium, platinum, copper, silver or gold, and most preferably Ru. Non-limiting examples of Ru-containing precursors are Ru metal, either unsupported (e.g. Ru black, Ru powder, Ru nanoparticles) or on supports such as activated carbon, silicon dioxide, aluminium oxides, titanium dioxide, zirconium dioxide, calcium carbonate, barium sulphate, activated charcoal, silicates, or zeolites, triruthenium dodecacarbonyl ($Ru_3(CO)_{12}$), ruthenium pentacarbonyl ($Ru(CO)_5$), and ruthenium oxide ($RuO_2$).

Preferred Ru-containing precursors are compounds in which Ru is in the Ru(II) or Ru(III) oxidation state; non-limiting examples are $RuBr_3$, $RuCl_3$, tricarbonyl-dichlororuthenium(II) dimer ($[RuCl_2(CO)_3]_2$), tricarbonyldibromoruthenium(II) dimer ($[RuBr_2(CO)_3]_2$, carbonylchlorohydridotris(triphenylphosphine)ruthenium (II) and Ru(II) and Ru(III) complexes containing ligands such as carbonyl (CO), bromide, chloride, iodide, fluoride, water, carboxylates (e.g. formate, acetates), β-diketonates (e.g. acetylacetonate), phosphines (e.g. triphenylphosphine, tricyclohexylphosphine, BINAP), carbenes (e.g. N-heterocyclic), aromatics (e.g. benzene, toluene, mesitylene, paracymene), cyclopentadienyls, cyclooctadiene, alkoxides, alkenes, alkynes, amines, polyamines, heteroaromatics, bipyridines, terpyridines, hybrid phosphine amines, pincer ligands (e.g. PCP-type, PNP-type), porphyrins, or sulfonamides. These compounds can be used in anhydric form or as hydrates containing one or more equivalents of water per Ru atom. Other examples of Ru precursors are compounds synthesized from the aforementioned compounds. The catalyst can also be a mixture of different Ru compounds.

Parameters for optimalisation in the reaction of the invention and which may also depend on the nature of the oxygenated compound comprise, but are not limited to: nature and amount of the ionic liquid; whether it is supported (e.g. SILP's) or not; temperature; $H_2$ pressure; amount and nature of acidic compound; amount and nature of Ru precursor; amount and origin of CO; presence and amount of solvent or co-solvent; mode of operation (batch or continuous).

The reaction temperature is advantageously between 140° C. and 280° C., preferably between 160° C. and 240° C. and even more preferably between 180° C. and 220° C. The $H_2$ pressure is advantageously between 0 and 200 bar, preferably between 10 and 70 bar and even more preferably between 30 and 60 bar.

The amount of acid compound is advantageously between 0 and 100 mol % (relative to the substrate), preferably between 1 and 20 mol % and even more preferably between 2 and 10 mol %.

The amount of Ru catalyst is advantageously between 0 and 20 mol % (relative to the substrate), preferably between 0.1 and 10 mol % and even more preferably between 0.5 and 5 mol %.

In some embodiments of the invention, the external addition of carbon monoxide (CO) to the reaction system has an advantageous effect on catalysis. Apart from addition of CO itself, also carbon monoxide-releasing molecules (CO-RMs) such as aldehydes, carboxylic acids or metal carbonyls can be used. Non-limiting examples of aldehydes are formaldehyde, acetaldehyde, propionaldehyde, butyraldehyde, 3-oxobutanal, benzaldehyde, furfural, hydroxymethylfurfural, cinnamaldehyde and vanillin. Non-limiting examples of carboxylic acids are formic acid, acetic acid, propionic acid, butyric acid, acrylic acid, lactic acid, citric acid and benzoic acid. Non-limiting examples of metal carbonyls are triruthenium dodecacarbonyl ($Ru_3(CO)_{12}$), tricarbonyldichlororuthenium(II) dimer ($[RuCl_2(CO)_3]_2$), ruthenium pentacarbonyl ($Ru(CO)_5$), carbonylchlorohydridotris(triphenylphosphine)ruthenium(II), vanadium hexacarbonyl ($V(CO)_6$), molybdenum hexacarbonyl ($Mo(CO)_6$), chromium hexacarbonyl ($Cr(CO)_6$), tungsten hexacarbonyl ($W(CO)_6$), dimanganese decacarbonyl ($Mn_2(CO)_{10}$), dirhenium decacarbonyl ($Re_2(CO)_{10}$), iron pentacarbonyl (Fe $(CO)_5$), triiron dodecacarbonyl, diiron nonacarbonyl ( ), dicobalt octacarbonyl ($Co_2(CO)_8$) and nickel tetracarbonyl ($Ni(CO)_4$). Alternatively, CO can be incorporated in the metal catalyst in a pretreatment step, in which the metal precursor is contacted with a CO releasing molecule, of which multiple examples have been mentioned above, at high temperature before reaction, in the ionic liquid, in another solvent or in the absence of a solvent. This pretreatment can be performed under an inert or a $H_2$ atmosphere and with or without acid. One non-limiting example of a pretreatment method is heating $RuBr_3$ to 210° C. for 1 h in the presence of formaldehyde, $Bu_4PBr$ and 40 bar $H_2$. Alternatively, CO can also be released in the reaction conditions from the oxygenated compound substrate or from reaction intermediates formed from the oxygenated compound.

In some embodiments of the invention, a solvent or, if the ionic liquid functions as solvent, a co-solvent can be used. The co-solvent can be miscible or immiscible with the ionic liquid. Preferably, the solvent is not miscible with the ionic liquid phase; non-limiting examples are hydrocarbons such as alkanes, alkenes, alkynes and aromatics.

The reaction described in the present invention can be performed batchwise or as a continuous process. For each mode of operation, a suitable reactor should be used. The present invention will now be illustrated by means of the Examples described below

EXAMPLES

All reactions were performed in a glass liner with a Teflon stopper in stainless steel pressure reactors. Except for the reactions of glycerol, the yield of apolar products in each reaction was investigated by gas chromatography of the dodecane phase immediately after cooling after reaction. The yield of polar compounds was investigated by derivatization using N,O-bis(trimethylsilyl)trifluoroacetamide (BSTFA) and GC analysis of the dodecane phase. In the reaction of glycerol, the volatile products were analysed via gas phase FTIR spectroscopy. Afterwards, dodecane was added and the yield of other compounds was investigated as usual.

Examples 1-10

0.5 mmol erythritol, 1.7 mmol tetrabutylphosphonium bromide ($Bu_4PBr$), 0.01 mmol metal catalyst, 0.025 mmol HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to 200° C. for 4 h. The conversion of erythritol was >99% in all cases. The yields of the most important products are shown in Table 1. The highest butene yields in these conditions were obtained with $RuCl_3$ as catalyst.

TABLE 1

| | | Yield (%) | | | |
|---|---|---|---|---|---|
| Example | Metal | Butane | Butenes | Furan | Butanone | 2,3-Butanedione |
| 1 | No | 0 | 0 | 6 | <1 | 20 |
| 2 | Ru/C | 2 | 3 | 6 | 10 | 0 |
| 3 | $RuCl_3$ | 8 | 49 | 7 | 8 | 0 |
| 4 | Rh/C | 3 | 0 | 6 | 33 | 0 |
| 5 | $RhCl_3$ | 1 | 0 | 2 | 29 | 0 |
| 6 | Pd/C | 1 | 0 | 9 | 19 | 0 |
| 7 | $PdCl_2$ | 3 | 0 | 2 | 39 | 0 |
| 8 | $IrCl_3·3H$ | 1 | 3 | 6 | 30 | 0 |
| 9 | Pt/C | 3 | 2 | 5 | 8 | 13 |
| 10 | $PtCl_2$ | 1 | 1 | 3 | 11 | 5 |

Examples 11-20

0.5 mmol erythritol, 1.7 mmol tetrabutylphosphonium bromide ($Bu_4PBr$), 0.01 mmol Ru catalyst, 0.025 mmol HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to 200° C. for 4 h. The conversion of erythritol was >99% in all cases. The yields of the most important products are shown in Table 2. The highest butene yields in these conditions were obtained with $[Ru(p-cym)Cl_2]_2$, $[RuCl_2(CO)_3]_2$ and $RuBr_3$ as catalyst.

TABLE 2

| | | Yield (%) | | | |
|---|---|---|---|---|---|
| Example | Metal | Butane | Butenes | Furan | Butanone |
| 11 | $Ru/Al_2O_3$ | 0 | 0 | 4 | 1 |
| 12 | Ru/C | 2 | 3 | 0 | 10 |
| 13 | $RU_3(CO)_{12}$ | 1 | 4 | 6 | 6 |
| 14 | $(PPh_3)_3RuCl_2$ | 32 | 17 | 2 | 1 |
| 15 | $Ru(Cp)_2$ | 0 | 20 | 6 | 1 |
| 16 | $[Ru(p-cym)Cl_2]_2$ | 6 | 54 | 5 | 4 |
| 17 | $[RuCl_2(CO)_3]_2$ | 0 | 57 | 5 | 3 |
| 18 | $RuCl_3$ | 8 | 49 | 7 | 8 |
| 19 | $RuBr_3$ | 3 | 55 | 5 | 8 |
| 20 | $Ru(acac)_3$ | 26 | 12 | 5 | 6 |

Example 21

0.5 mmol erythritol, 1.7 mmol tetrabutylphosphonium chloride ($Bu_4PCl$), 0.01 mmol $RuBr_3$, 0.025 mmol HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to 200° C. for a period of 4 h. The conversion of erythritol was >99%. The main product was 1,4-anhydroerythritol (51% yield). 8% Butane was formed. No butenes were detected.

Examples 22-27

0.5 mmol erythritol, different amounts of tetrabutylphosphonium bromide ($Bu_4PBr$), 0.01 mmol $RuBr_3$, different amounts of HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to the 200° C. for 2 h. The conversion of erythritol was >99% in all cases. The yields of the most important products are shown in Table 3. The best butene yields are obtained between 1 and 1.7 mmol $Bu_4PBr$.

TABLE 3

| | $Bu_4PBr$ | Yield (%) | | | |
|---|---|---|---|---|---|
| Example | (mmol) | Butane | Butenes | Furan | Butanone |
| 22 | 1 | 3 | 48 | 6 | 17 |
| 23 | 1.125 | 3 | 47 | 6 | 20 |
| 24 | 1.375 | 4 | 46 | 7 | 21 |
| 25 | 1.6 | 4 | 43 | 7 | 20 |
| 26 | 1.7 | 4 | 46 | 6 | 21 |
| 27 | 3.4 | 2 | 30 | 8 | 33 |

Examples 28-31

0.5 mmol erythritol, 1.7 mmol tetrabutylphosphonium bromide ($Bu_4PBr$), 0.01 mmol $RuBr_3$, 0.025 mmol of the indicated acid and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to the 200° C. for 2 h. The conversion of erythritol was >99% in all cases. The yields of the most important products are shown in Table 4. Except for $H_2SO_4$, similar butene yields are obtained for all acids.

TABLE 4

| Example | Acid | Yield (%) | | | |
|---|---|---|---|---|---|
| | | Butane | Butenes | Furan | Butanone |
| 28 | HBr | 3 | 46 | 6 | 23 |
| 29 | $H_2SO_4$ | 0 | 22 | 7 | 34 |
| 30 | Nafion | 2 | 49 | 6 | 17 |
| 31 | Silicotungstic acid | 3 | 47 | 7 | 24 |

Examples 32-36

0.5 mmol erythritol, 1.7 mmol tetrabutylphosphonium bromide ($Bu_4PBr$), the indicated amount of $RuBr_3$, 0.025 mmol HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to the 200° C. for 2 h. The conversion of erythritol was >99% in all cases. The yields of the most important products are shown in Table 5. The highest yield is achieved for 3 mol % $RuBr_3$. In the reaction using 1 mol % $RuBr_3$, no overreduction to butane occurs.

TABLE 5

| Example | $RuBr_3$ (mol %) | Yield (%) | | | |
|---|---|---|---|---|---|
| | | Butane | Butenes | Furan | Butanone |
| 32 | 0 | 0 | 0 | 6 | 1 |
| 33 | 0.5 | 0 | 21 | 7 | 34 |
| 34 | 1 | 0 | 34 | 5 | 33 |
| 35 | 2 | 4 | 46 | 6 | 23 |
| 36 | 3 | 6 | 58 | 6 | 14 |

Examples 37-40

0.5 mmol erythritol, 1.7 mmol tetrabutylphosphonium bromide ($Bu_4PBr$), 0.005 mmol $RuBr_3$, 0.025 mmol HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to the indicated temperature for 2 h. The conversion of erythritol was >99% in all cases. The yields of the most important products are shown in Table 6. The highest butene yields were obtained at 210° C. and 220° C.

TABLE 6

| Example | Temperature (° C.) | Yield (%) | | | |
|---|---|---|---|---|---|
| | | Butane | Butenes | Furan | Butanone |
| 37 | 180 | 0 | 4 | 5 | 29 |
| 38 | 200 | 0 | 34 | 5 | 33 |
| 39 | 210 | 0 | 43 | 6 | 18 |
| 40 | 220 | 0 | 43 | 6 | 13 |

Examples 41-45

0.5 mmol erythritol, 1.7 mmol tetrabutylphosphonium bromide ($Bu_4PBr$), 0.005 mmol $RuBr_3$, 0.5 mmol HBr and 1 mL of dodecane with 0.5 mmol tetradecane as internal standard were added to the reactor. The reactor was flushed 3 times with $N_2$ and 3 times with $H_2$. Then the reactor was loaded with the indicated $H_2$ pressure and heated to 210° C. for 2 h. The conversion of erythritol was >99% in all cases. The yields of the most important products are shown in Table 7. The highest butene yields were obtained with 40 and 46 bar $H_2$.

TABLE 7

| Example | $H_2$ (bar) | Yield (%) | | | |
|---|---|---|---|---|---|
| | | Butane | Butenes | Furan | Butanone |
| 41 | 0 | 0 | 0 | 4 | 1 |
| 42 | 20 | 0 | 10 | 4 | 21 |
| 43 | 30 | 0 | 21 | 4 | 21 |
| 44 | 40 | 0 | 43 | 6 | 18 |
| 45 | 46 | 0 | 43 | 7 | 14 |

Examples 46-51

0.5 mmol erythritol, 1.7 mmol tetrabutylphosphonium bromide ($Bu_4PBr$), 0.005 mmol $RuBr_3$, the indicated amount of HBr and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to 210° C. for 2 h. The conversion of erythritol was >99% in all cases. The yields of the most important products are shown in Table 8. The highest butene yields were obtained with 2.5 mol % HBr.

TABLE 8

| Example | HBr (mol %) | Yield (%) | | | |
|---|---|---|---|---|---|
| | | Butane | Butenes | Furan | Butanone |
| 46 | 0 | 4 | 25 | 9 | 28 |
| 47 | 2.5 | 0 | 47 | 9 | 19 |
| 48 | 5 | 0 | 43 | 6 | 18 |
| 49 | 6 | 0 | 41 | 6 | 16 |
| 50 | 7.5 | 0 | 40 | 5 | 13 |
| 51 | 10 | 0 | 38 | 5 | 18 |

Examples 52-60

0.5 mmol erythritol, 1.7 mmol tetrabutylphosphonium bromide ($Bu_4PBr$), the indicated amount of Ru catalyst and formaldehyde (37 wt % in water), 5 mol % HBr (except for example 60, which was performed with 10 mol % HBr) and 1 mL of dodecane with 0.5 mmol tetradecane as internal standard were added to the reactor. The reactor was flushed 3 times with $N_2$ and 3 times with $H_2$. Then the reactor was loaded with 40 bar $H_2$ and heated to 200° C. (examples 52 and 53 to 210° C.) for the indicated time. The conversion of erythritol was >99% in all cases. The yields of the most important products are shown in Table 9. The highest butene yields were obtained using either 3 mol % [$RuCl_2(CO)_3$] or 5 mol % $RuBr_3$ together with 0.4 mmol formaldehyde.

TABLE 9

| Example | Catalyst | Time (h) | Yield (%) | | |
|---|---|---|---|---|---|
| | | | Butane | Butenes | Butanone |
| 52 | 1 mol % $RuBr_3$ | 2 | 0 | 43 | 18 |
| 53 | 1 mol % $RuBr_3$ + 0.01 mmol HCOH | 2 | 0 | 18 | 21 |

TABLE 9-continued

| Example | Catalyst | Time (h) | Yield (%) Butane | Butenes | Butanone |
|---|---|---|---|---|---|
| 54 | 2 mol % RuBr$_3$ | 4 | 3 | 55 | 8 |
| 55 | 2 mol % RuBr$_3$ + 0.05 mmol HCOH | 4 | 0 | 50 | 2 |
| 56 | 5 mol % RuBr$_3$ | 2 | 4 | 52 | 13 |
| 57 | 5 mol % RuBr$_3$ + 0.4 mmol HCOH | 2 | 0 | 66 | 1 |
| 58 | 1 mol % [RuCl$_2$(CO)$_3$]$_2$ | 4 | 0 | 20 | 16 |
| 59 | 2 mol % [RuCl$_2$(CO)$_3$]$_2$ | 4 | 0 | 57 | 3 |
| 60 | 3 mol % [RuCl$_2$(CO)$_3$]$_2$ | 4 | 0 | 64 | 0 |

Examples 61-67

The indicated amount of RuBr$_3$ and formaldehyde (37 wt % in water), 1.7 mmol tetrabutylphosphonium bromide (Bu$_4$PBr) and 5 mol % HBr were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol erythritol and 1 mL of dodecane with 0.5 mmol tetradecane as internal standard were added to the reactor. The reactor was again flushed 3 times with N$_2$ and 3 times with H$_2$. Then the reactor was loaded with 40 bar H$_2$ and heated to 180° C. for the indicated time. The conversion of erythritol was >95% in all cases. The yields for the most important products are shown in Table 10. Butane was not detected in any of these reactions.

TABLE 10

| Example | RuBr$_3$ (mol %) | HCOH (mmol) | Time (h) | Yield (%) Butenes | Butanone | Hydroxy compounds |
|---|---|---|---|---|---|---|
| 61 | 2 | 0.08 | 2 | 11 | 2 | 45 |
| 62 | 2 | 0.16 | 2 | 14 | 8 | 52 |
| 63 | 2 | 0.32 | 2 | 8 | 1 | 62 |
| 64 | 2 | 0.16 | 4 | 40 | 3 | 31 |
| 65 | 2 | 0.16 | 6 | 52 | 3 | 18 |
| 66 | 3 | 0.24 | 2 | 22 | 3 | 45 |
| 67 | 3 | 0.24 | 4 | 63 | 1 | 11 |

Example 68

0.01 mmol RuBr$_3$ (2 mol %), 0.16 mmol formaldehyde (37 wt % in water), 1.7 mmol tetrabutylphosphonium bromide (Bu$_4$PBr) and 0.025 mmol HBr (5 mol %) were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol glycerol was added to the reactor. The reactor was again flushed 3 times with N$_2$ and 3 times with H$_2$. Then the reactor was loaded with 40 bar H$_2$ and heated to 210° C. for 2 h. The conversion of glycerol was >99%. The yields for the most important products are shown in Table 11.

TABLE 11

| Yield (%) | | |
|---|---|---|
| Propene | Acetone | Hydroxy compounds |
| 90 | 3 | 1 |

Example 69-71

0.015 mmol RuBr$_3$ (3 mol % in Examples 69 and 70, 5 mol % in Example 71), 0.24 mmol formaldehyde (37 wt % in water), 1.7 mmol tetrabutylphosphonium bromide (Bu$_4$PBr) and 0.0375 mmol HBr (7.5 mol %) were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol xylitol and 1 mL of dodecane with 0.5 mmol tetradecane as internal standard were added to the reactor. The reactor was again flushed 3 times with N$_2$ and 3 times with H$_2$. Then the reactor was loaded with 40 bar H$_2$ and heated to the indicated temperature for the indicated time. The conversion of xylitol was >99%. The yields for the most important products are shown in Table 12. Less than 1% pentane was detected in Examples 69 and 70. 3% pentane was formed in Example 71. B=butenes, PEN=pentenes, CP=cyclopentene, GVL=gamma-valerolactone, PA=pentanoic acid, PEA=pentenoic acids, LA=levulinic acid and AHX=anhydroxylitols.

TABLE 12

| Ex. | T (° C.) | time | Yield (%) B | PEN | CP | GVL | PA | PEA | LA | AHX |
|---|---|---|---|---|---|---|---|---|---|---|
| 69 | 180 | 16 | 3 | 39 | 2 | 0 | 10 | 4 | 0 | 5 |
| 70 | 200 | 6 | 10 | 34 | 3 | 3 | 10 | 5 | 10 | 0 |
| 71 | 210 | 4 | 13 | 56 | 5 | 0 | 17 | 1 | 0 | 0 |

Example 72-74

0.015 mmol RuBr$_3$ (3 mol %), 0.24 mmol formaldehyde (37 wt % in water), 1.7 mmol tetrabutylphosphonium bromide (Bu$_4$PBr) and the indicated amount of HBr were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol sorbitol and 1 mL of dodecane with 0.5 mmol tetradecane as internal standard were added to the reactor. The reactor was again flushed 3 times with N$_2$ and 3 times with H$_2$. Then the reactor was loaded with 40 bar H$_2$ and heated to the indicated temperature for 8 h. The conversion of sorbitol was >99%. The yields for the most important products are shown in Table 13. No hexane was detected. MCP=1-methylcyclopentene. DMTHF=2,5-dimethyltetrahydrofuran, Ph=phenol, HA=hexanoic acid, HEA=hexenoic acids, AHS=monoanhydrosorbitols and (mostly) isosorbide.

TABLE 13

| Example | HBr (mol | T (° C. | Yield (%) Hexenes | MCP | DMTH | P | H | HE | AH |
|---|---|---|---|---|---|---|---|---|---|
| 72 | 5 | 180 | 6 | 8 | 4 | 2 | 6 | 1 | 38 |
| 73 | 5 | 200 | 12 | 13 | 0 | 3 | 5 | 10 | 1 |
| 74 | 7.5 | 200 | 14 | 12 | 0 | 3 | 7 | 8 | 0 |

Examples 75-76

0.01 mmol RuBr$_3$ (2 mol %), 0.16 mmol formaldehyde (37 wt % in water), 1.7 mmol tetrabutylphosphonium bromide (Bu$_4$PBr) and the indicated amount of HBr were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol levulinic acid and 1 mL of dodecane with 0.5 mmol tetradecane as internal standard were added to the reactor. The reactor was again flushed 3 times with N$_2$ and 3 times with H$_2$. Then the reactor was loaded with 40 bar H$_2$ and heated to the indicated temperature for 2 hours. The yields for the most important products are shown in Table 14. B=butenes, PEA=pentenoic acids, PA=pentanoic acid, GVL=gamma-valerolactone.

TABLE 14

| Example | HBr (mol) | T (° C.) | Yield (%) | | | | Conversion (%) |
| --- | --- | --- | --- | --- | --- | --- | --- |
| | | | B | PEA | PA | GVL | |
| 75 | 3 | 180 | 1 | 13 | 2 | 49 | 82 |
| 76 | 5 | 200 | 5 | 14 | 5 | 52 | 88 |

Example 77

0.01 mmol RuBr$_3$ (2 mol %), 0.16 mmol formaldehyde (37 wt % in water), 1.7 mmol tetrabutylphosphonium bromide (Bu$_4$PBr) and 0.015 mmol HBr (3 mol %) were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol furfural and 1 mL of dodecane with 0.5 mmol tetradecane as internal standard were added to the reactor. The reactor was again flushed 3 times with N$_2$ and 3 times with H$_2$. Then the reactor was loaded with 40 bar H$_2$ and heated to 180° C. for 2 hours. The conversion of furfural was >99%. The yields for the most important products are shown in Table 15.

TABLE 15

| Yield (%) | | | | |
| --- | --- | --- | --- | --- |
| Butenes | Pentenoic | Pentanoic | GVL | Levulinic acid |
| 1 | 9 | 2 | 31 | 26 |

Example 78

0.01 mmol RuBr$_3$ (2 mol %), 0.16 mmol formaldehyde (37 wt % in water), 1.7 mmol tetrabutylphosphonium bromide (Bu$_4$PBr) and 0.015 mmol HBr (3 mol %) were added to a reactor. The reactor was flushed 3 times with N$_2$ and 3 times with H$_2$. Then the reactor was loaded with 40 bar H$_2$ and heated to 210° C. for 1 hour. The reactor was cooled on ice and 0.5 mmol 5-(hydroxymethyl)furfural and 1 mL of dodecane with 0.5 mmol tetradecane as internal standard were added to the reactor. The reactor was again flushed 3 times with N$_2$ and 3 times with H$_2$. Then the reactor was loaded with the 40 bar H$_2$ and heated to 180° C. for 2 hours. The conversion of 5-(hydroxymethyl)furfural was >99%. The yields for the most important products are shown in Table 16.

TABLE 16

| Yield (%) | | |
| --- | --- | --- |
| 2,5-DimethylTHF | 2,5-Dimethylfuran | Hexadienes |
| 26 | 4 | 3 |

The invention claimed is:

1. A method of hydrodeoxygenation of oxygenated compounds into compounds with unsaturated carbon-carbon bonds, the method comprising:
reacting a reaction mixture under a H$_2$ atmosphere at acidic conditions at a temperature from 180° C. to 250° C. and a pressure from 10 bar to 200 bar, the reaction mixture comprising:
an oxygenated compound containing one or more of a hydroxyl, a keto group, or an aldehyde group;
an ionic liquid comprising an ionic liquid cation and an ionic liquid anion;
a homogeneous metal catalyst; and
carbon monoxide or a carbon monoxide releasing compound.

2. The method according to claim 1, wherein the reaction mixture comprises a carbon monoxide releasing compound, and the carbon monoxide releasing compound is formaldehyde.

3. The method according to claim 1, wherein the oxygenated compound is a sugar or a sugar alcohol.

4. The method according to claim 1, wherein the ionic liquid cation is a phosphonium.

5. The method according to claim 1, wherein the ionic liquid cation is tetrabutylphosphonium.

6. The method according to claim 1, wherein the ionic liquid anion is bromide.

7. The method according to claim 1, wherein the homogeneous metal catalyst is metallic ruthenium or a compound comprising Ru(II) or Ru(III).

8. The method according to claim 1, wherein the reaction mixture comprises a carbon monoxide releasing compound, and the carbon monoxide releasing compound is an aldehyde, a carboxylic acid, or a metal carbonyl.

9. The method according to claim 1, wherein the reaction mixture comprises a carbon monoxide releasing compound, and the carbon monoxide releasing compound is a metal carbonyl and comprises the homogeneous metal catalyst.

* * * * *